US00PP20145P2

(12) United States Plant Patent
van der Spek

(10) Patent No.: US PP20,145 P2
(45) Date of Patent: Jun. 30, 2009

(54) ***HYDRANGEA* PLANT NAMED 'SIDASAND'**

(50) Latin Name: *Hydrangea macrophylla*
Varietal Denomination: Sidasand

(76) Inventor: Daniel van der Spek, Nieuwkoopseweg 45, 2631 PP Nootdorp (NL)

( * ) Notice: Subject to any disclaimer, the term of this patent is extended or adjusted under 35 U.S.C. 154(b) by 0 days.

(21) Appl. No.: 11/903,265

(22) Filed: Sep. 22, 2007

(51) Int. Cl.
*A01H 5/00* (2006.01)

(52) U.S. Cl. ..... Plt./250

(58) Field of Classification Search ..... Plt./250
See application file for complete search history.

*Primary Examiner*—Annette H Para
*Assistant Examiner*—Louanne C Krawczewicz Myers

(57) ABSTRACT

A new and distinct *Hydrangea* cultivar named 'Sidasand' is disclosed, characterized by white flowers with purple margins, slow to moderate growth habit and a compact inflorescence. The new variety is a *Hydrangea,* and naturally blooms from April through September.

1 Drawing Sheet

Latin name of the genus and species: *Hydrangea macrophylla.*
Variety denomination: 'Sidasand'.

BACKGROUND OF THE INVENTION

The new cultivar is a product of a planned breeding program. The intent of this breeding program is to produce stronger pot plant varieties with attractive flower colors. The new variety was discovered as seedling within the planned breeding program. This seedling is a result from the crossing of the female parent, an undistributed proprietary variety referred to as 9626 with the male parent, an undistributed proprietary variety referred to as 9659. The crossing was made by the inventor, Daniel van der Spek in the summer of 1999. 'Sidasand' was selected as a single plant by Daniel van der Spek in May of 2001 in Nootdorp, The Netherlands.

Asexual reproduction of the new cultivar 'Sidasand' by vegetative cuttings was performed in Nootdorp, The Netherlands and has shown that the unique features of this cultivar are stable and reproduced true to type through 6 successive generations.

SUMMARY OF THE INVENTION

The cultivar 'Sidasand' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Sidasand'. These characteristics in combination distinguish 'Sidasand' as a new and distinct *Hydrangea* cultivar:

1. Flattened inflorescence;
2. Unique petal coloration of white with purple margins;
3. Dark green foliage;
4. Strong plant, resisting breaking in production and post-harvest situations.

Plants of the new cultivar 'Sidasand' are similar to plants of the female parent, '9626' in most horticultural characteristics, however, plants of the new cultivar 'Sidasand' differ from '9626' in the following characteristics;

1. Flower color of 'Sidasand' is white with a purple margin whereas '9626' is solid light pink.
2. 'Sidasand' has more flowers per inflorescence.
3. 'Sidasand' has a wider inflorescence.
4. 'Sidasand' is a shorter plant than '9626.'

Plants of the new cultivar 'Sidasand' are similar to plants of the male parent, '9659' in most horticultural characteristics, however, plants of the new cultivar 'Sidasand' differ from '9659' in the following characteristics;

1. Foliage color of 'Sidasand' is darker than '9659.'
2. 'Sidasand' is a shorter plant.
3. Flowers of 'Sidasand' have a distinctive darker margin whereas '9659' has solid color flowers.

Plants of the new cultivar 'Sidasand' are similar to plants of the commercial variety 'Snow,' distributed and unpatented in the United States. However, plants of the new cultivar 'Sidasand' differ from 'Snow' in the following characteristics;

1. Foliage of 'Sidasand' is much more resistant to stress than 'Snow.'
2. 'Sidasand' flowers have a distinctive red/purple margin whereas flowers of 'Snow' are solid white.
4. 'Sidasand' plants produce roots faster than 'Snow.'

BRIEF DESCRIPTION OF THE PHOTOGRAPH

The accompanying photograph in FIG. 1 illustrates in full color a typical blooming plant of 'Sidasand' grown in a greenhouse. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'Sidasand' plants grown in a greenhouse in Brielle, The Netherlands from October 2005 to October 2006. The growing temperature ranged from 16° C. to 17° C. at night to 18° C. to 20° C. during the day. The pH of the growing medium was between 5.0 and 5.5. 'Sidasand' has not been tested for the effect of Aluminum on stem, leaf and flower colors. Measurements and numerical values represent averages of typical flowering types.

Botanical classification: *Hydrangea macrophylla* cultivar 'Sidasand.'

PROPAGATION

Time to rooting: 19 to 21 days at approximately 20° C.
Root description: Fine, fibrous.

PLANT

Growth habit: Flowering perennial shrub.
Height: Approximately 38 cm from soil level to the top of the infloresence.
Blooming period: Naturally blooming April through September.
Plant spread: Approximately 48.5 cm.
Growth rate: Moderate.
Branching characteristics: Moderately free branching.
Length of lateral branches: Approximately 25.3 cm.
Number of lateral branches: Approximately 11.
Diameter of lateral branches: Approximately 0.5 cm.
Pinching required: Yes.
*Details of pinching.*—The first pinch is given at 8 weeks from the planting of a rooted cutting. A second pinch is given 12 weeks from planting a rooted cutting.
Lateral branch shape: Round.
Lateral ranch texture: Leathery.
Lateral branch strength: Very strong.
Lateral branch color: Approximately RHS Yellow-Green 144A, slightly tinged at the nodes with RHS Greyed-Purple 183B.
Other stem or plant characteristics: Stems covered with lenticels at a density of approximately 5.5 lenticels per square cm.
*Lenticel length.*—Approximately 0.16 cm.
*Lenticel width.*—Approximately 0.075 cm.
*Lenticel color.*—About RHS Greyed-Purple 183B.
Number of leaves per lateral branch: Average 8
Age of plant described: Approximately 1 year.

FOLIAGE

Leaf:
*Arrangement.*—Opposite.
*Compound or single.*—Single
*Average length.*—Approximately 12.1 cm.
*Average width.*—Approximately 7.3 cm.
*Shape of blade.*—Oval to elliptic oblong.
*Apex.*—Apiculate.
*Base.*—Acuminate.
*Attachment.*—Stalked.
*Margin.*—Serrate, approximately 2 teeth per cm.
*Texture of top surface.*—Moderately glossy, non-pubescent.
*Texture of bottom surface.*—Matte, non-pubescent.
*Leaf internode length.*—Approximately 6.38 cm.
*Color.*—Young foliage upper side: Near R.H.S. Green 141B. Young foliage under side: Near R.H.S. Green 143A. Mature foliage upper side. Near R.H.S. Green 139A. Mature foliage underside: Near R.H.S. Green 138B.
*Venation.*—Type: Pinnate Venation color upper side: Near R.H.S. Yellow-Green 145A. Venation color under side: Near R.H.S. Yellow-Green 145B.
*Durability of foliage to stresses.*—High.
Petiole:
*Average length.*—Approximately 2.2 cm.
*Diameter.*—Approximately 0.4 cm.
*Color.*—Near R.H.S. Yellow-Green 145B.

FLOWER

Bloom period:
*Natural season.*—Continuous April through September.
Inflorescence:
*Arrangement.*—Terminal.
*Type.*—Flattened compound corymb.
*Height.*—Approximately 6.8 cm.
*Width.*—Approximately 15.3 cm.
*Quantity of flowers per inflorescence.*—Fertile flowers, approximately 180.
Sterile Flowers, approximately 15.
Bud:
*Bud shape* (*sterile flowers*).—Obovate.
*Bud length* (*sterile flowers*).—Approximately 0.45 cm.
*Bud diameter* (*sterile flowers*).—Approximately 0.3 cm.
*Bud color* (*sterile flowers*).—Near R.H.S. Red-Purple 65D, top darker, Red-Purple 65A. Base/calyx. Near R.H.S. Yellow-Green 146C.
*Bud shape* (*fertile flowers*).—Globose.
*Bud length* (*fertile flowers*).—Approximately 0.3 cm.
*Bud diameter* (*fertile flowers*).—Approximately 0.3 cm.
*Bud color* (*fertile flower*).—Near R.H.S. Yellow-Green 144B.
Flower:
*Shape.*—Rotate.
*Facing direction.*—All directions, with the majority facing outward.
*Quantity of flowers per lateral stem.*—Approximately 195.
*Quantity of flowers and buds per plant.*—Approximately 1950.
*Diameter of entire flower.*—Fertile; Approximately 0.9 cm. Sterile: Approximately 4.1 cm.
*Depth of flower.*—Fertile; Approximately 0.6 cm. Sterile: Approximately 1.2 cm.
*Rate of opening.*—Individual flowers: Fully open approximately 4 days from the bud stage. Whole Plant: Approximately 50% of flowers open at once.
*Flower longevity on plant.*—Fertile flowers: Approximately 5 days. Sterile flowers: Approximately 35 days.
*Persistent or self-cleaning.*—Persistent.
*Fragrance.*—No.
Petals:
*Length of petal.*—Approximately 4.5 cm.
*Width of petal.*—Approximately 2.5 cm.
*Apex.*—Acute.
*Base.*—Cordate.
*Shape of petal.*—Ovate.

*Petal margin.*—Entire.
*Petal arrangement.*—Rotate.
*Petal number.*—Average 5.
*Petals fused.*—No.
*Petal Appearance.*—Dull.
*Petal texture* (*both surfaces*).—Smooth.

Color:
*Upper surface at first opening.*—Near White 155A and Red-Purple 69D, top margin near Red-Purple 67A.
*Upper surface at maturity.*—Near White 155A and Red-Purple 69C, top margin near Red-Purple 67A.
*Upper surface at fading.*—Near Red-Purple 69C.
*Under surface at first opening.*—Near White 155A and Red-Purple 69D.
*Under surface at maturity.*—Near White 155A and Red-Purple 69D, top margin near Red-Purple 67B.
*Under surface at fading.*—Near Red-Purple 58B.

Petaloids: No.
Fragrance: None.

CALYX

Present: Yes.
Shape: Rotate, lower ¾ fused.
Length: Approximately 0.35 cm.
Diameter: Approximately 0.45 cm.

SEPAL

Sepals: Only sterile flowers have sepals.
Number: Average 5.
Sepal texture (both surfaces): Smooth.
Sepal arrangement: Rotate.
Sepal length: Approximately 0.35 cm.
Sepal width: Approximately 0.1 cm.
Sepal shape: Deltoid.
Base: Fused into a tube ⅔ of length.
Apex shape: Acute.
Margin: Entire.
Color: Upper side near R.H.S. Yellow-Green 146D. Under side near R.H.S. Yellow-Green 146C, base Yellow-Green 146D.

PEDUNCLE

Length: Approximately 4.8 cm.
Diameter : Approximately 0.38 cm
Angle: Approximately 25 degrees (0 degrees=straight upright)
Strength: Strong
Color: Near R.H.S. Yellow-Green 144C.

PEDICEL

Present: Yes.
Length (sterile flowers): Approximately 2.7 cm.
Diameter (sterile flowers): Approximately 0.11 cm.
Angle (sterile flowers): Approximately 10 degrees.
Strength (sterile flowers): Strong.
Color (sterile flowers): Near White 155A, base Greyed-Purple 187C.
Length (fertile flowers): Approximately 1 cm.
Diameter (fertile flowers): Approximately 0.08 cm.
Angle (fertile flowers): Approximately 15 degrees.
Strength (fertile flowers): Moderate.
Color (fertile flowers): Near White 155A.

REPRODUCTIVE ORGANS

*Number of pistils per flower.*—3.
*Pistil length.*—Approximately 0.15 cm.
*Stigma shape.*—Lobed.
*Stigma color.*—Near Red-Purple 57D.
*Style color.*—Near Red-Purple 62D.
*Style length.*—Approximately 0.08 cm.
*Ovary color.*—Near Yellow-Green 154C.
*Stamens.*—Average 10.
*Anther shape.*—Broad kidney-shaped.
*Anther size.*—11 cm.
*Anther color.*—Near White 155A, filament colored Red-Purple 62C.
*Pollen color.*—Near White 155A.
*Pollen quantity.*—Very low.

OTHER CHARACTERISTICS

Disease/resistance: Neither resistance nor susceptibility to diseases or pests has been observed in this variety.
Drought/tolerance and cold tolerance: Semi-hardy perennial, tolerant of some high temperatures. Upper limit of temperature tolerance has not been observed, however, known to tolerate temperatures of at least up to 40° C. Lower limits have also not been observed, however, observed hardy to −15° C. No drought tolerance has been observed.
Fruit/seed production: No fruits/seeds detected to date.
Effect of aluminum added to the growing medium: 'Sidasand' has not been tested for the effect of Aluminum on stem, leaf and flower colors.

What is claimed is:

1. A new and distinct cultivar of *Hydrangea* plant named 'Sidasand' as herein illustrated and described.

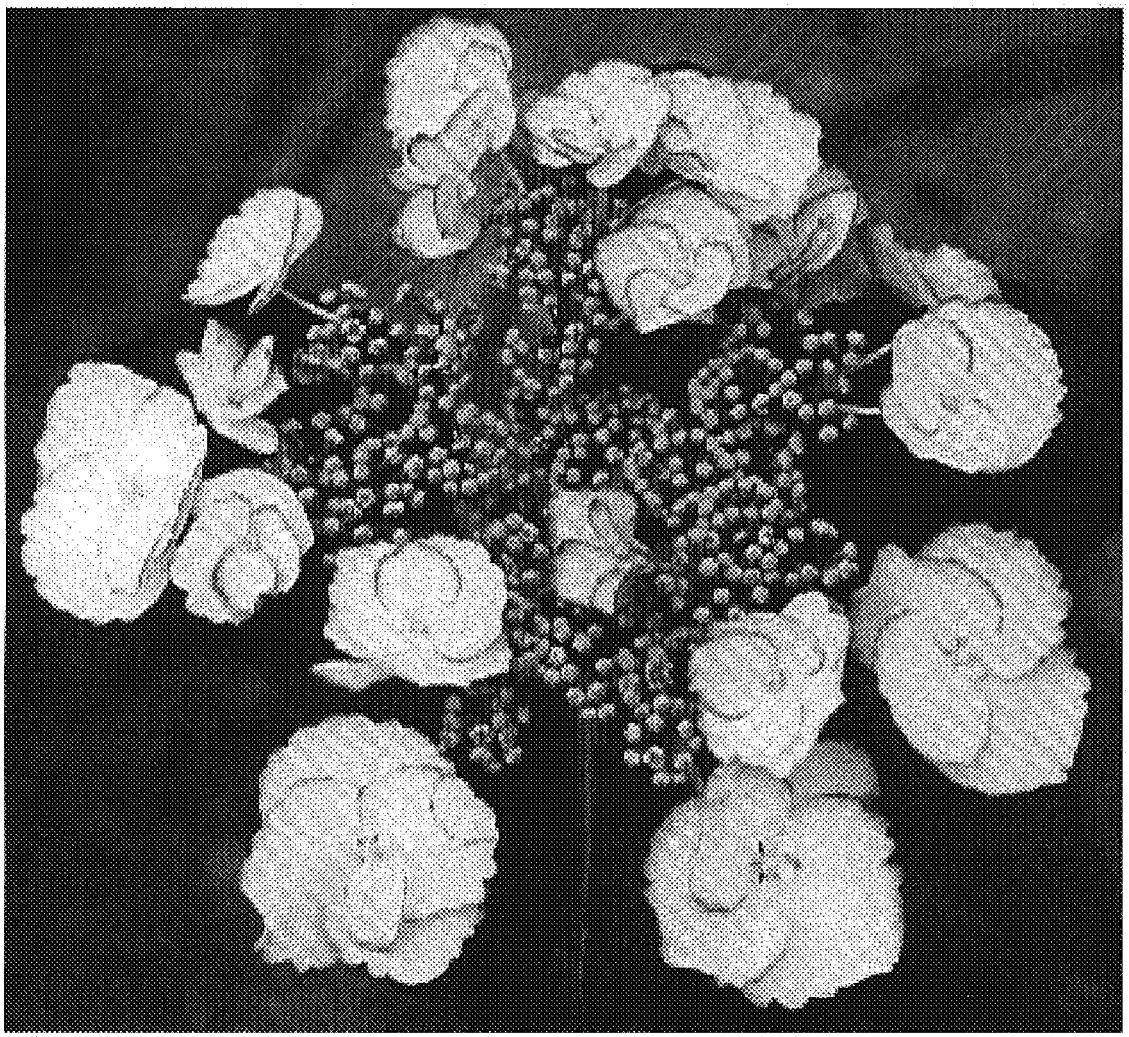

* * * * *